(12) United States Patent
Zagury et al.

(10) Patent No.: US 8,101,165 B2
(45) Date of Patent: *Jan. 24, 2012

(54) USE OF IMMUNOGENS TO TREAT OR PREVENT, IN MALIGNANT TUMORS, THE IMMUNE OR VASCULAR DISORDERS INDUCED BY EXTRACELLULAR FACTORS

(75) Inventors: Jean Francois Zagury, Paris (FR); Bernard Bizzini, Paris (FR); Helene Le Buanec, Paris (FR); Daniel Zagury, Paris (FR)

(73) Assignee: Neovacs, Paris (FR)

( * ) Notice: Subject to any disclaimer, the term of this patent is extended or adjusted under 35 U.S.C. 154(b) by 661 days.

This patent is subject to a terminal disclaimer.

(21) Appl. No.: 11/735,319

(22) Filed: Apr. 13, 2007

(65) Prior Publication Data

US 2008/0031849 A1    Feb. 7, 2008

Related U.S. Application Data

(62) Division of application No. 10/344,253, filed as application No. PCT/FR01/02575 on Aug. 8, 2001, now abandoned.

(30) Foreign Application Priority Data

Aug. 9, 2000  (FR) ..................... 00 10480

(51) Int. Cl.
*A61K 38/19* (2006.01)
*A61K 38/00* (2006.01)
*C07K 5/00* (2006.01)
*C07K 14/52* (2006.01)

(52) U.S. Cl. ...... 424/85.1; 514/19.2; 530/300; 530/345; 530/351

(58) Field of Classification Search ....................... None
See application file for complete search history.

(56) References Cited

U.S. PATENT DOCUMENTS 6,093,405 A * 7/2000 Zagury et al. .............. 424/198.1
6,805,865 B1 10/2004 Holaday et al.

FOREIGN PATENT DOCUMENTS

| WO | WO 92/22577 | * 12/1992 |
| WO | WO 94/02167 | 2/1994 |
| WO | WO 96/10423 | 4/1996 |
| WO | WO 97/09064 | 3/1997 |

OTHER PUBLICATIONS

Srivastava, *Curr. Opinion in Immunol.*, 18:201-205 (2006).
Rosenberg et al, *J. Immunology*, 163:1690-1695 (1999).
Kargiotis et al., *J. Neuro-Oncol.*, 78(3):281-293 (2006).

* cited by examiner

*Primary Examiner* — Elizabeth C Kemmerer
*Assistant Examiner* — Xiaozhen Xie
(74) *Attorney, Agent, or Firm* — Browdy and Neimark, PLLC

(57) ABSTRACT

The invention concerns vaccines comprising as an active principle an immunogen which is a cytokinetic factor or a cell regulating factor particularly transcriptional or another type of factor with immunosuppressive/apoptotic/angiogenic properties abnormally released in the extracellular (stromal) environment by cancer or stromal cells of malignant tumors, and a pharmaceutically acceptable carrier for inducing a systemic or mucosal immune response with secretory formation of class IgC or IgA neutralizing antibodies directed against the native factor, or which is derived from such a factor and the use of said immunogen to obtain a medicine for use as anticancer drug.

4 Claims, 2 Drawing Sheets

USE OF IMMUNOGENS TO TREAT OR PREVENT, IN MALIGNANT TUMORS, THE IMMUNE OR VASCULAR DISORDERS INDUCED BY EXTRACELLULAR FACTORS

CROSS-REFERENCE TO RELATED APPLICATIONS

The present application is a division of application Ser. No. 10/344,253, filed Aug. 28, 2003, now abandoned, which is a 371 national stage application of PCT/FR01/02575, filed Aug. 8, 2001, which claims priority from FR0010480, filed Aug. 9, 2000. The entire contents of these applications are incorporated herein by reference.

BACKGROUND OF THE INVENTION

1. Field of the Invention

The present invention relates to the use of medicamentous vaccine preparations with a therapeutic or prophylactic use intended to treat or prevent, in malignant tumors, immune disorders in particular immunosuppression and apoptosis of the immune or vascular cells such as angiogenesis, induced by extracellular factors, cytokines or other regulation factors in particular transcriptional factors, abnormally produced by the cancer cells or the stromal cells.

2. Description of the Related Art

Conventional treatments of cancers whether they are of viral origin, induced by retroviruses, or EBV or HPV or also the hepatitis viruses, or of chronic origin, due to asbestos or to benzene derivatives, whether they are of epithelial (carcinomas) or conjunctive (sarcomas) type or also of the blood (lymphomas) comprise the surgical removal of tumors usually combined with chemotherapy and/or radiotherapy.

Although effective for certain cancers, particularly when carried out in the early stages, these often poorly tolerated treatments are inadequate and relapses and metastases compromise the progress of patients.

This is why when scientists in the 80's and 90's cloned and purified tumor-associated antigens (TAA) or tumor-specific antigens (TSA) in cancer cells originating from numerous malignant tumors (cancer of the breast, prostate, colon and rectum, cervix, ATL lymphoma), numerous experiments and clinical trials of anti-cancer vaccination (Dvorak E. Experimental design for vaccine preparations against human malignant tumors. Med Hypotheses (1986) 20:429-52, Houghton A N. On course for a cancer vaccine. Lancet (1995) 345:1384-5, Herlyn D, Linnenbach A, Koprowski H, Herlyn M. Epitope- and antigen-specific cancer vaccines. Int Rev Immunol (1991) 7:245-57, antigen-specific cancer vaccines. Int Rev Immunol (1991) 7:245-57, Ostankovitch M, Choppin J, Guillet J G. Tumor cell antigenicity: cancers and vaccines. Rev Prat (1995) 45:1921-6, Zhu M Z, Marshall J, Cole D, Schlom J, Tsang K Y. Specific cytolytic T-cell responses to human CEA from patients immunized with recombinant avipox-CEA vaccine. Clin Cancer Res (2000) 6:24-33, Tsunoda T, Tanimura H, Yamaue H, Tanaka H, Matsuda K. Tumor specific CTL therapy for advanced cancer and development for cancer vaccine. Hepatogastroenterology (1999) 46:1287-92), using TAA and TSA as antigens were carried out, aiming to specifically destroy the malignant cells which carry these antigens thanks to the action of killer cells, particularly cytolytic lymphocytes (CTL), carriers of specific receptors, induced by the vaccinal immune reaction.

Clinical trials using such vaccines carried out in patients carrying different tumors (melanoma, cancer of the breast, colorectal cancer, cancer of the bladder etc.) have made it possible to establish the following facts:

The anti-cancer vaccine preparations containing the tumorous antigens (TAA or TSA) presented in different forms have been well tolerated and have generally not caused regional or systemic complications.

Such vaccine preparations can induce in patients an immune reaction of CTL type (Tsunoda T, Tanimura H, Yamaue H, Tanaka H, Matsuda K. Tumor specific CTL therapy for advanced cancer and development for cancer vaccine. Hepatogastroenterology (1999) 1:1287-92, Schwaab T, Heaney J A, Schned A R, Harris R D, Cole B F, Noelle R J, Phillips D M, Stempkowski L, Ernstoff M S. A randomized phase II trial comparing two different sequence combinations of autologous vaccine and human recombinant interferon gamma and human recombinant interferon alpha2B therapy in patients with metastatic renal cell carcinoma: clinical outcome and analysis of immunological parameters. J Urol (2000) 163:1322-7, Steller M A, Gurski K J, Murakami M, Daniel R W, Shah K V, Celis E, Sette A, Trimble E L, Park R C, Marincola F M. Cell-mediated immunological responses in cervical and vaginal cancer patients immunized with a lipidated epitope of human papillomavirus type 16 E7. Clin Cancer Res (1998) 4:2103-9, capable in vitro of specifically destroying the cellular targets which carry TAA or TSA epitopes complexed with the Major Histocompatibity Complex.

On the other hand, to date, no phase III clinical trial has been able to show that these vaccine preparations, aiming to specifically destroy the cancerous cells by the differentiation of killer cells, were effective.

Therefore, since 1992, after Levine (The p53 tumor suppressor gene and gene product. Princess Takamatsu Symp (1989) 20:221-30) as well as other scientific teams had showed that the native p53 protein which has reparative effects on the DNA strands and immunosuppressive effects on the cell cycle or a mutant of this protein was abundantly produced and accumulated in malignant tumors, the same Levine proposes carrying out a vaccination using the p53 protein, appearing to be a tumor-associated antigen (TAA). This was presented at the surface of dendritic cells (DC) or added into a bacterial vector (BCG type) in such a way as to induce an immune reaction of CTL type directed against the cancerous cells (See also WO-A-94/02167).

In support of this patent application, scientific publications show the beneficial role of killer cells and the pejorative role of specific antibodies in the development of malignant tumors (Theobald M, Biggs J, Dittmer D, Levine A J, Sherman L A. Targeting p53 as a general tumor antigen. Proc Natl Acad Sci USA (1995) 92:11993-7, Roth J. et al, p53 as a target for cancer vaccines: recombinant canarypox virus vectors expressing p53 protect mice against lethal tumor cell challenge, 1996, Proc Natl Acad Sci USA.; 93:4781-6).

Following Levine, other teams modifying the vector or the adjuvant of the p53 immunogen have filed ten or so patent applications on the use of new galenic formulations of anti-p53 vaccine also aiming to induce the formation of CTL killer T cells targeting the cancer cells expressing the p53 protein.

The experimental trials associated with these anti-p53 vaccines have shown the innocuousness and the immunogenicity assessed by the appearance of anti-p53 killer cells. In addition, the only clinical trial of anti-p53 vaccination which has been carried out and published confirmed the innocuousness and the immunogenicity of the vaccine. However no phase III trial has been able to validate the effectiveness of this vaccine strategy.

The Applicant surprisingly discovered that the immunosuppression and the angiogenesis of the microenvironment of cells infected by some viruses such as HIV-1 and the microenvironment of cancerous cells provide a rational explanation for the lack of effectiveness of these vaccine strategies, as these previous strategies target the cancerous cell and not the disturbance of its microenvironment.

Now, to date the treatments have all aimed to directly kill the cancer T cells themselves, this is to say the parenchymetous cells, the Applicant has found that it was just as judicious or even more judicious to combat the molecules produced in the extracellular (stromal) microenvironment of the tumor and encouraging the development of the latter.

It should be remembered that any tissue or tumor is formed from parenchymetous cells which bathe in a microenvironment called stroma. This stroma is itself constituted by stromal cells (which can be immune, endothelial, or fibroblastic cells) and an extracellular medium.

The works of the Applicant have shown in fact that soluble factors secreted by the cells infected by HIV-1, in particular the Tat protein or by the immune cells of patients infected by HIV in particular IFNα and TGFβ or produced by cancer cells, such as the E7 protein of HPV in cancer of the cervix or the Tax protein of HTLV1 in the ATL leukaemias or the p53 protein in colorectal cancer, had immunosuppressive properties capable of inhibiting the cellular immune reactions in tumors and because of this explained the ineffectiveness of previous vaccines.

Bibliographical study has made it possible to confirm these observations by the Applicant, confirming the presence of immunosuppressive factors released into the extracellular medium of malignant tumors:

Some of these as yet unidentified factors were produced by colorectal cancer cells (Ebert E C, Roberts Al, O'Connell S M, Robertson F M, Nagase H. Characterization of an immunosuppressive factor derived from colon cancer cells. J Immunol. (1987) 138:2161-8 or Remacle-Bonnet M M, Pommier F J, Kaplanski S, Rance R J, Depieds R C. Inhibition of normal allogenic lymphocyte mitogenesis by a soluble inhibitor extracted from human colonic carcinoma. J Immunol (1976) 117:1145-51, glioblastoma cells (29-Fontana A, Hengartner H, de Tribolet N, Weber E. Glioblastoma cells release interleukin 1 and factors inhibiting interleukin 2-mediated effects. J Immunol. (1984) 132:183744), melanomas (30.Hersey P, Bindon C, Czerniecki M, Spurling A, Wass J, McCarthy W H. Inhibition of interleukin 2 production by factors released from tumor cells. J Immunol. (1983) 131:2837-42), or malignant ascites (Tamura K, Shibata Y, Matsuda Y, Ishida N. Isolation and characterization of an immunosuppressive acidic protein from ascitic fluids of cancer patients. Cancer Res. (1981) 41:3244-52, Oh S K, Moolten F L. Non specific immunosuppressive factors in malignant ascites: further characterization and possible relationship to erythrocyte receptors of human peripheral T cells. J Immunol. (1981) 127:2300-7).

Other transcriptional regulation factors, as reported above, are of cellular origin such as the p53 protein, accumulated in some malignant tumors, in particular colorectal tumors (Remvikos Y, Tominaga O, Hammel P, Laurent-Puig P, Salmon R J, Dutrillaux B, Thomas G. Increased p53 protein content of colorectal tumors correlates with poor survival. Br J Cancer 1992 66:758-64, Gan H, Ouyang Q, Wang Y. Expression of p53 protein in colorectal cancer and its relationship to cell proliferative activity and prognosis. Chung Hua Chung Liu Tsa Chih (1996) 18:244-6). The p53 protein, released by active transport by the secretion pathways not using the peptide signal or by passive diffusion is present in the extracellular medium, and it has been isolated by chromatography on glass fibre from serum from cancer patients (Zusman I, Sandier B, Gurevich P, Zusman R, Smirnoff P, Tendler Y, Bass D, Shani A, Idelevich E, Pfefferman R, Davidovich B, Huszar M, Glick J. Comparative study of the role of serum levels of p53 antigen and its tumor cell concentration in colon cancer detection. Hum Antibodies Hybridomas. (1996):123-8, Sandler B, Smirnoff P, Tendelr Y, Zinder O, Zusman R, Zusman I. Specificity of polyclonal anti-p53 IgG for isolation of the soluble p53 antigen from human serum. Int J Mol. Med. 1998 1:767-70).

SUMMARY OF THE INVENTION

Cytokines, such as TGFβ a well known immunosuppressant; VEGF angiogenic growth factor, pro-inflammatory IL-6 or IL-10 equally immunosuppressive, are abnormally secreted and released in the extracellular medium of some cancerous cells. The Applicant has itself shown that the cells of the cancerous cell line SiHa, just like the DU145 cells of cancer of the prostate and the MT2 cells of leukaemia cell lines abnormally produce and release cytokines such as VEGF and/or IL-6 in the extracellular medium whilst the RAJ1 cells of leukaemia cell lines secrete IL-10 in the extracellular medium.

In this context, a subject of the present invention is the use as an anticancer medicament of new vaccine preparations without toxicity intended to neutralize:

either immunosuppressive, apoptotic or angiogenic cytokines produced in excess in the extracelluar stromal compartment by the cancerous or stromal cells of malignant tumors. The examples of anti-cytokine vaccines described in EP-591.281 particularly concerned anti-IFNα vaccines used against AIDS and other immune disorders.

or cell regulation factors, particularly transcriptional factors or other factors with immunosuppressive, apoptotic or angiogenic properties abnormally produced in the extracellular stromal compartment by the cancerous cells. The examples of immunogens described in WO-A-00/03732 are derived from regulation factors of viral origin such as the E7 proteins of HPV 16, Tax proteins of HTLV-1 and Tat proteins of HIV-1.

In these new non-toxic vaccine preparations, the immunogen

1—is constituted by cytokinic factors or derived from cytokinic factors or from cell regulation factors particularly transcriptional factors or other factors with immunosuppressive/apoptotic/angiogenic properties abnormally produced by the cancerous or stromal cells of malignant tumors in the extracellular medium.

2—is preferably presented in a galenic form allowing an immune reaction to be induced preferentially inducing IgG and/or IgA class antibodies capable of locally antagonising the immunosuppressive/apoptotic/angiogenic factors abnormally present in the extracellular medium of the tumors and to inhibit the effects of them.

DETAILED DESCRIPTION OF THE INVENTION

Figure 1:
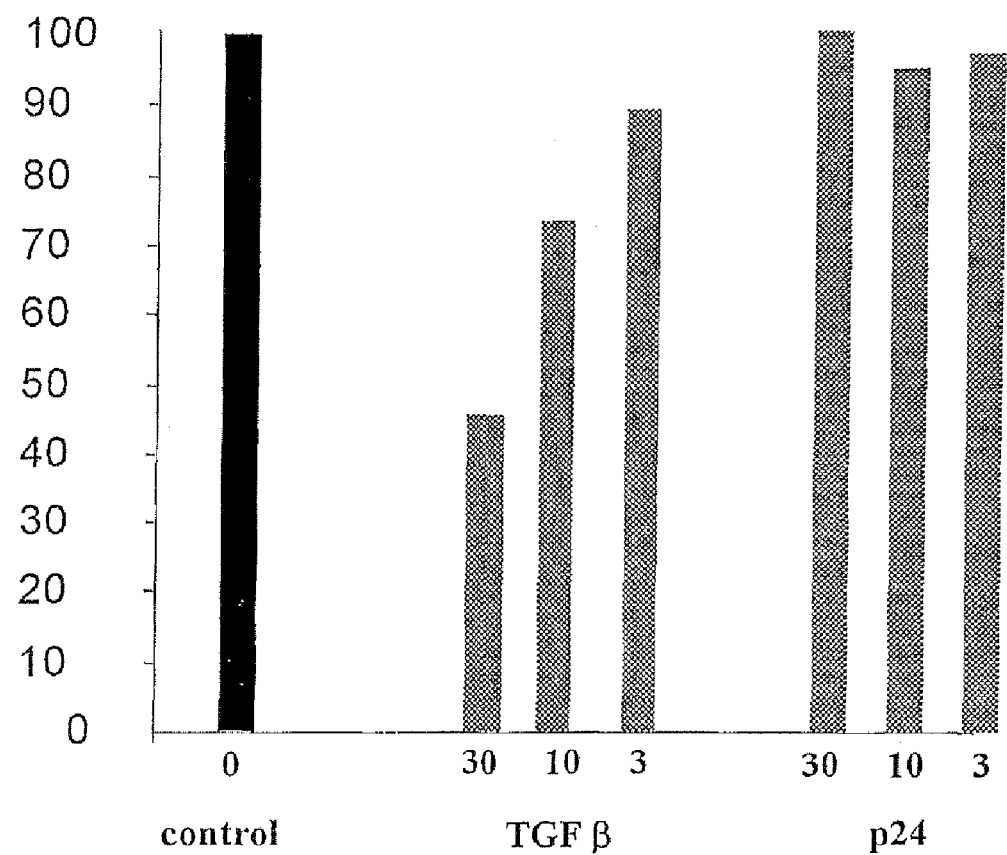
FIG. 1 shows the inhibition of cell proliferation by the TGFβ expressed in % of cell proliferation ((control cpm/sample cpm)×100) at three concentrations (30, 10 and 3 ng/ml) of TGFβ and p24 protein. The control corresponds to a concentration of recombinant protein used equal to 0.

The present invention proposes in particular the use as anticancer medicament of vaccines particularly directed against pathogenic factors produced abnormally in the extracellular matrix of malignant tumors and in particular
- the TGFβ protein: TGFβ being a major immunosuppressive cytokine produced by numerous cancer cells;
- the IL-10 protein: IL-10 also being a major immunosuppressive cytokine
- the p53 protein: If the p53 regulation protein produced abnormally by the cancer cells and accumulated in the tumors can represent a tumor-associated antigen (TAA) as has been shown in the prior art, the Applicant has discovered that it can also act in its extracellular configuration as an immunosuppressive and apoptogenic factor on the immune cells as illustrated hereafter in the examples.
- VEGF, growth factor of the endothelial cells: VEGF cytokine being a major cytokine of angiogenesis, activating the proliferation of the endothelial cells.
- IL-6, IFNγ and TNFα, pro-inflammatory cytokines also participate in the angiogenesis process, by activating the expression of the adhesion molecules of the endothelial cells (ICAM, VCAM, E selectin).

All of these vaccines aim to induce an immune reaction with the formation of IgG class antibodies (for all cancers) and above all IgA class antibodies (for epithelial cancers) in such a way as to locally neutralize, in the tumor, the particularly immunosuppressive/apoptotic/angiogenic pathogenic factors and to block their effects, therefore allowing natural immunity or a vaccine directed against the TAA or TSA antigens to function normally and to eliminate the diseased cells.

That is why a subject of the present Application is a vaccine characterized in that it contains, as active ingredient, an immunogen which is a factor or which is derived from a cytokinic factor or a particularly transcriptional cell regulation factor or from another type of factor with immunosuppressive/apoptotic/angiogenic properties abnormally produced by the cancerous or stromal cells of malignant tumors, as well as a pharmaceutically acceptable excipient allowing the induction of a systemic or mucosal immune reaction with the formation of antibodies of IgG or secretory IgA class directed against the native factor and more particularly a vaccine characterized in that it contains, as active ingredient, an immunogen which is
- a cytokinic factor or a particularly transcriptional cell regulation factor or another type of factor with immunosuppressive/apoptotic/angiogenic properties abnormally released in the extracellular (stromal) medium by the cancerous cells or the stromal cells of malignant tumors, as well as a pharmaceutically acceptable excipient allowing the induction of a systemic or mucosal immune reaction with the formation of neutralizing antibodies of IgG or secretory IgA class directed against the native factor,
- or which is derived from such a factor,
with the exception of:
- IL-6, a fragment of IL-6 or an analogue of IL-6 in a form producing non-mucosal immunity and not conjugated to a carrier protein such as KLH,
- a p53 epitope too short to be immunogenic and conjugated to a carrier protein such as KLH,
- a composition of a p53 protein or p53 peptide, IL12 and an adjuvant.

Under preferential conditions of implementation, the immunogen derived from a cytokinic factor or from a particularly transcriptional cell regulation factor or from another type of factor with immunosuppressive/apoptotic/angiogenic properties abnormally produced by the cancer or stromal cells of malignant tumors by chemical, physical treatment, by genetic mutation, by adjuvant conditioning or is the product of a genetic vaccination (DNA vaccine) or is a proteinic or peptidic fragment of such a factor or is also derived from such a proteinic or peptidic fragment.

The immunogen will preferably be conjugated to a carrier protein.

In fact the Applicant has discovered that such a measure increases the number of auxiliary (helper) sites and because of this increases the antibody response neutralizing the extracellular factor targeted.

Under yet more preferential conditions of implementation the immunogen derived from a cytokinic factor or from a particularly transcriptional cell regulation factor or from another type of factor with immunosuppressive/apoptotic/angiogenic properties abnormally produced by the cancerous or stromal cells of malignant tumors or from a proteinic or peptidic fragment of such a factor by conjugation to a carrier protein which is KLH.

Under other preferential conditions of implementation, the immunogen is chosen from TGFβ, IL-10, p53 protein, VEGF, IL-6, IFNα, IFNγ, the Fas ligand and TNFα or is a derivative of them.

The immunogen of these vaccine preparations, without toxicity like any other medicament, can be derived from an immunosuppressive/apoptotic/angiogenic factor or from one of its peptidic fragments by chemical, physical treatment by genetic mutation, by adjuvant conditioning or be the product of a genetic vaccination (DNA vaccine). Such immunogen treatments which have been described in WO-A-00/03732 can be used in the present invention to obtain a vaccine without any toxicity and in particular without any immunosuppressive character. But the immunogens can also be used in their native state.

Chemical treatments consist, for example, of detoxifying the native or recombinant protein by a treatment with aldehydes in particular formaldehyde, monofunctional aldehyde and therefore not acting by conjugating molecules, in accordance with the detoxification of tetanic or diphtheritic toxins, or also consist of treatments blocking the sulfidryl groups, such as carboxyamidation, maleimidation or carboxymethylation or in any other treatment blocking other aminated residues as described in previous applications by the Applicant.

Under yet other preferential conditions of implementation, the immunogen is a mutant of the native factor or a fragment of the native factor.

A mutant of the factor possessing at least 70%, preferably at least 80% and very particularly at least 90% homology with the native proteinic factor or also a proteinic or peptidic fragment of the factor could be used. In the case of a peptide, this will preferably be carried by a carrier protein such as KLH or the tetanic toxoid. A carrier protein could also advantageously be used in the case of the native proteinic factor or also a proteinic factor of the latter.

The products described above used as immunogens, with the exception of the native factors, are new, or at least the majority of them are. They therefore enter into the scope of the invention.

The physical treatments can be carried out by heat, U.V. radiation, X rays or contact with an atmosphere rich in $O_2$. These physical treatments generating intramolecular modifications between chemical radicals (thiol groups for example), can in an appropriate manner change the conformation of the molecule, functionally inactivate it whilst conserving its immunogenic properties.

Genetic modifications can be obtained by genetic engineering carrying out insertions, deletions or substitutions of residues. The genetic mutants could undergo or not undergo an additional chemical and/or physical treatment. The modified proteins above can for example be prepared from a protein having an identical or similar sequence to a peptide sequence of a factor above. All of these processes are well known in the state of the art.

A DNA vaccine (genetic vaccination) could consist of a plasmid comprising an expression promoter gene such as that of CMV and the gene coding for an immunogen defined above (native factor or derivative i.e. fragments).

By "is derived" or "to be derived" from immunosuppressive/apoptotic/angiogenic factors, it is also meant that the immunogenic compound can be constituted by all or a fragment of the starting protein or even less notably be conjugated to a carrier protein such as KLH (keyhole limpet hemocyanin) or tetanus toxoid, directly or preferably by a bifunctional coupling reagent.

It can comprise one or more modifications in the amino acids of this protein or fragment such as deletions, substitutions, additions, or functionalizations such as acylation of amino acids, insofar as these modifications remain within the context specified above (absence of toxicity, immunological character). For example, in general the replacement of a leucine residue by an isoleucine residue does not modify such properties; the modifications must generally concern less than 40% of the amino acids, in particular less than 30% preferably less than 20% and quite particularly less than 10% of the proteinic factor. It is important that the modified protein or fragment is not denatured as can be carried out for example by a physical treatment such as heat in order to preserve its conformational sites so that the antibodies induced by the modified derivatives are active vis à vis the native protein.

Generally speaking, as regards the modifications, the homology or the similarity between the modified immunogen and the native immunosuppressive protein or protein part, as well as the dimensions of the immunogenic compound, similarly the methods of use, or conjugation of the immunogenic compound according to the invention to an immunogenic protein such as tetanic toxoid, reference may be made in particular to WO-A-86/06 414 or to EP-A-0.220.273 or also to PCT/US.86/00831 or equivalents.

A fragment can comprise from 8 to 110 amino acids for example, preferably from 20 to 110, in particular from 12 to 60, particularly from 25 to 60, more particularly from 12 to 40 and quite particularly from 30 to 50 amino acids. Such a fragment can also comprise one or more C or N terminal sides of 1 to 5 additional amino acids i.e. different from the segment of origin. A fragment must, moreover, comprise at least one cysteine to be able to be the subject of carboxymethylation.

A proteinic factor could comprise all of the amino acids of the native sequence, with less than 25 amino acids, preferably less than 15 amino acids, particularly less than 10 amino acids and quite particularly less than 5 amino acids, indeed even a single amino acid deleted.

For adjuvant conditioning, the immunogen can in particular be included in a water-in-oil emulsion, using for example ISA 51.

A vaccine preparation containing the anti immunosuppressive/apoptotic/angiogenic immunogen can be administered in an appropriate galenic form to induce an immune response of systemic type by intramuscular (IM), subcutaneous (SC), intradermic (ID) or of mucosal type route by intranasal, oral, vaginal or rectal route.

A vaccine preparation containing the anti immunosuppressive/apoptotic/angiogenic immunogen can also contain other immunogens, such as the TAA or TSA cancer antigens or adjuvants such as cytokines or, CTB or Lt mutant (LTµ) type enterotoxin proteins (Freytag L C, Clements J D, Bacterial toxins as mucosal adjuvants Curr Top Microbiol Immunol; (1999) 236:215-36).

A galenic preparation for systemic use, administered by SC, IM, ID route, can be a water emulsion containing the immunogen, in oil, or a suspension of calcium phosphate in which the immunogen is included, or aluminium hydroxide adsorbing the immunogen.

A galenic preparation targeted at a mucosal immune response administered preferentially by nasal or oral route, but also by vaginal or rectal route, above all for boosters, can in particular be constituted by biodegradable polymer microspheres, such as slow-release form PLGs (poly(lactide-co-glycolides)), PLAs ((poly(lactides)) and PCLs, (poly(epsi-lon-caprolactones)) (Baras B. et al, Single-dose mucosal immunization with biodegradable microparticles containing a *Schistosoma mansoni* antigen. Infect Immun. (1999) 67:2643-8) in which are included the antigen molecules, aqueous suspensions of calcium phosphate including or adsorbing the antigen, nanoparticles, such as chitosan nanoparticles.

The vaccine preparations could be packaged for the intranasal route in the form of a gel with carbopol as excipient, nasal drops or spray and for oral route in the form of gastroresistant capsules, sugar-coated pills or gastroresistant granules.

In the case of DNA vaccine administered by systemic or mucosal route, the galenic formulation of the plasmid can be a suspension in a physiological liquid such as physiological PBS (phosphate buffer=PBS). The plasmids could be included in biodegradable polymer (PLG, PLA, PCL) microspheres and administered in gastroresistent capsules for ingestion (oral route). The DNA can also be expressed in a living bacterial vector of *salmonella* type or adenovirus or poxvirus type.

A subject of the present application is also the use as immunogen of a factor which is a cytokinic factor or a particularly transcriptional cell regulation factor or another type of factor with immunosuppressive/apoptotic/angiogenic properties abnormally released in the extracellular (stromal) medium by cancerous or stromal cells of malignant tumors or which are derived from such a factor.

A subject of the present application is also the use of an immunogen which is a factor or which is derived from a cytokinic factor or from a particularly transcriptional cell regulation factor or from another type of factor with immunosuppressive/apoptotic/angiogenic properties abnormally produced by the cancerous cells or stromal cells of malignant tumors for obtaining a medicament intended for a use as an anticancer medicament by a mechanism of reducing the effects, on the microenvironment of said cancerous or stromal cells of malignant tumors, of a cytokinic factor or a particularly transcriptional cell regulation factor or another type of factor with immunosuppressive/apoptotic/angiogenic properties abnormally produced by said cancerous or stromal cells of malignant tumors.

Finally, a subject of the present application is an immunogen which is a factor or which is derived from a cytokinic factor or from a particularly transcriptional cell regulation factor or from another type of factor with immunosuppressive/apoptotic/angiogenic properties abnormally released in the extracellular medium by the cancerous or stromal cells of malignant tumors for its use in a method of therapeutic treatment of the human or animal body, i.e. as a medicament, in particular a curative or preventative vaccine.

The immunogens which are a subject of the present invention have very useful pharmacological properties. They are endowed in particular with remarkable antagonist, reducing, inhibitory or in particular neutralizing properties, of immunosuppressive/apoptotic/angiogenic properties of factors abnormally produced in the extracellular (stromal) medium by the cancerous or stromal cells of malignant tumors unlike compounds of the prior art which act directly on the cancer cells of malignant tumors.

These properties are illustrated hereafter in the experimental part. They justify the use of the vaccines and immunogens described above as a medicament.

The medicaments according to the present invention are of use for example in treatment which is both curative and preventative of cancers of epithelial origin such as for example colorectal cancer, cancer of the prostate, cancer of the breast and of connective origin such as sarcomas or originating from the blood such as Epstein-Barr type lymphomas or leukaemias.

A subject of the present application is also a process of active immunization of patients characterized in that an immunogen compound as defined above is used as immunogen advantageously combined with an adjuvant of mineral, oily or of synthetic immunity, or also an immunogenic compound as defined above, advantageously conjugated for example using a dialdehyde or combined with a protein increasing its immunogenicity.

These immunizations can be carried out both as a curative and a preventative measure.

The preferential conditions of implementation of the above-described vaccines also apply to the other subjects of the invention aimed at above.

The following examples illustrate the present invention.

Example 1

Vaccine Based on the VEGF Immunogen Intended to Induce a Systemic Immune Reaction with Preferential Formation of IgG Class Specific Antibodies The vaccine is formed from a water in oil emulsion constituted by 50% ISA 51 (Seppic, Paris) and 50% of an aqueous solution of VEGF (20 to 200 µg/dose).

Example 2

Vaccine Based on the Plasmid Immunogen for Systemic IL-10 Type DNA Vaccination

The plasmids coding for IL-10 (50 to 200 µg/dose) are suspended in 0.2 to 1 ml of PBS for intramuscular administration.

Example 3

Vaccine Based on p53 Immunogen Intended to Induce a Mucosal Type Immune Reaction with Preferential Formation of IgA Class Anti-p53 Antibodies p53 immunogen (20 to 100 µg/dose) is inserted into a calcium phosphate gel in the presence or not in the presence of LTµ adjuvant (5 to 20 µg/dose) for intranasal instillation. The preparation is administered by intranasal route either in the form of nasal drops, or in the form of a gel by adding carbopol.

Example 4

Vaccine Based on IL-10 Immunogen Intended to Induce an Immune Reaction of Mucosal Type Reaction with Preferential Formation of IgA Class Anti IL-10 Antibodies PLG microspheres containing the immunogen (100 to 300 µg/dose) and a mutant of the LT toxin (5-25 µg/dose) were prepared The inclusion of IL-10 and LTµ is carried out in biodegradable microspheres according to the protocol of Baras B. et al (Baras B. et al, Single-dose mucosal immunization with biodegradable microparticles containing a *Schistosoma mansoni* antigen. Infect Immun. (1999) 67:2643-8).

Example 5

Vaccine Based on IFNγ Plasmid Immunogen for Mucosal Type DNA Vaccination

The plasmids of IFNγ (100-500 µg/dose) in the presence of LTµ (5-20 µg/dose) are included in PLG microspheres according to the protocol described by Baras B. et al. Administration by oral route is carried out by gavage or by ingestion of gastroresistent capsules containing the microspheres and an alginate based excipient.

Example 6

Vaccine Based on VEGF Immunogen Intended to Induce a Systemic Immune Reaction with Preferential Formation of IgG Class Specific Antibodies The vaccine is formed from a water in oil emulsion constituted by 50% ISA 51 (SEPPIC) and 50% of an aqueous solution of VEGF (20 to 200 µg/dose).

The immunogen originates from Preparation 3 of VEGF stabilized by glutaraldehyde.

Example 7

Vaccine Based on VEGF Immunogen Conjugated to KLH Intended to Induce a Systemic Immune Reaction with Preferential Formation of IgG Class Specific Antibodies The vaccine is formed from a water in oil emulsion constituted by 50% ISA 51 (SEPPIC) and 50% of an aqueous solution of VEGF (20 to 200 µg/dose).

Example 8

Vaccine Based on E7 Immunogen of HPV16 Conjugated to KLH to Induce a Systemic Immune Reaction The vaccine is formed from a water in oil emulsion of 50% ISA (SEPPIC, Paris) and 50% of an aqueous solution of E7 conjugated to KLH (20 to 200 µg/dose).

The immunogens serving for the preparation of the vaccines above were prepared as follows:

Preparation 1: Anti IL-6 Immunogen

IL-6 immunogen derived from the recombinant IL-6 cytokine by treatment with formol followed by a treatment with glutaraldehyde:

28 µl of a formol solution (35%) diluted to 1/10 in sterile phosphate buffer is added to 1 ml of a solution of IL-6 at 1 mg/ml in sterile phosphate buffer. After adding merthiolate at 1/10,000, the mixture is placed for 9 days in an oven at 37° C. Glutaraldehyde is then added at a concentration of 0.0026 M. After 3 minutes, 100 µl of glycine at 50 mg/ml is added to the mixture to block the excess aldehyde groups and it is dialyzed against a large volume of phosphate buffer. In this way the immunogen is stabilized.

Characteristics of IL-6

The antigenicity of the treated recombinant IL-6 cytokine in comparison to that of the native recombinant protein was measured using an R&D ELISA test (D6050): the detoxified recombinant IL-6 cytokine presents an antigenicity equal to the antigenicity of the corresponding native protein.

The absence of toxicity in vitro is measured by a cell proliferation test. Mononucleated cells from human peripheral blood are cultured in the presence of the superantigen SEB and in the presence of a dose of the native or detoxified recombinant IL-6 protein corresponding to 10 times and 30 times the physiological dose of the native cytokine. Cell proliferation is expressed in % of cell proliferation [cpm (counts per minute) control/sample cpm]×100). The control corresponds to a concentration of recombinant protein used equal to 0. The results are presented in the following table:

|  |  | % cell proliferation |
| --- | --- | --- |
| Native IL-6 | 0 ng/ml | 100 |
| Native IL-6 | 30 ng/ml | 98 |
| Treated IL-6 | 30 ng/ml | 95 |

The treated IL-6 used at doses 10 times and 30 times greater than the physiological doses does not modify the proliferation of mononucleated cells of human peripheral blood activated by SEB.

Preparation 2: Anti-p53 Immunogen

The p53 immunogen was detoxified by treatment with formol according to the protocol described by Ramon (Ramon G, Sur le pouvoir floculant et les propriétés immunisantes d'une toxine diphtérique rendue anatoxique (anatoxine). C.r. hebd. Seances Acad. Sci. (1923) 177: 1338-1340), followed by a treatment of the p53 recombinant protein with glutaraldehyde (sc-4246, Santa Cruz) under the following conditions: 3 µl of a formol solution diluted to 1/100 in sterile phosphate buffer is added to 10 µl of a solution of native p53 at 1 mg/ml. The mixture is placed in an oven for 2 days at 37° C. 25 µl of glutaraldehyde at 1/100 is then added to it. After reacting for 15 minutes at room temperature, 2 µl of 2M glycine is added to block the excess aldehyde groups.

Characteristics of the p53 Immunogen

The antigenicity of the treated recombinant p53 protein in comparison to that of the native recombinant protein was measured using an ELISA test from Amersham Pharmacia Biotech (p53 Rapid Format Pantropic Human ELISA, VQIA26): The native and treated p53 proteins present an equivalent antigenicity.

Absence of toxicity in vitro: the treated p53 protein used in doses 10 times and 30 times greater than the physiological doses (0.5 to 5 ng/ml) does not modify the proliferation of mononucleated cells of the human peripheral blood activated by SEB or by the anti CD3 antibodies. Measurement of the proliferation was carried out by the $^3$H-thymidine test.

Preparation 3: Anti VEGF Immunogen

The VEGF immunogen derived from VEGF (293-VE-010; R&D) is obtained by treatment with glutaraldehyde under the following conditions: 5 µl of a solution of glutaraldehyde diluted to 1/500 in sterile phosphate buffer is added to 100 µl of a solution of native VEGF at 5 µg/ml in phosphate buffer. After reacting for 5 minutes at ambient temperature, 2 µl of 1M glycine is added to block the reaction.

Characteristics of VEGF

The antigenicity of the treated VEGF cytokine in comparison to that of the native recombinant cytokine was measured using an R&D ELISA test (DVE00): the native and treated cytokines present an equivalent antigenicity.

The absence of toxicity in vitro was measured using a cell proliferation test. Mononucleated cells from human peripheral blood are cultured in the presence of the superantigen SEB and in the presence of a dose of the native or treated recombinant VEGF protein corresponding to 10 times and 30 times the physiological dose of the native cytokine. The cell proliferation is expressed in % of cell proliferation ((control cpm/sample cpm)×100). The control corresponds to a concentration of recombinant protein used equal to 0. The results are presented in the following table:

|  |  | % cell proliferation |
| --- | --- | --- |
| Native VEGF | 0 ng/ml | 100 |
| Native VEGF | 30 ng/ml | 92 |
| Treated VEGF | 30 ng/ml | 97 |

The treated VEGF cytokine used at doses 10 times and 30 times greater than the physiological doses does not modify the proliferation of mononucleated cells of human peripheral blood activated by SEB.

Preparation 4: Anti TGFβ Immunogen

TGFβ immunogen derived from TGFβ is detoxified by treatment with formol according to the protocol described by Ramon (Ramon G, Sur le pouvoir floculant et les propriétés immunisantes d'une toxine diphthérique rendue anatoxique (anatoxine). C.r. hebd. Seances Acad. Sci. (1923) 177: 1338-1340), followed by a treatment with glutaraldehyde, in accordance with the protocol described for the p53 immunogen.

Characteristics of the TGFβ Immunogen

The antigenicity of the treated TGFβ cytokine in comparison to that of the native recombinant protein was measured using an R&D ELISA test (DB100): The native and treated TGFβ cytokines present an equivalent antigenicity.

The absence of toxicity of the treated TGFβ cytokine was measured by a T cell proliferation test described in Example A1. This test shows that the detoxified TGFβ used at physiological doses of 0.5 to 5 ng/ml does not reduce the proliferation of lymphocytes.

Preparation 5: Anti IL-10 Immunogen

A) IL-10 Immunogen Derived from IL-10 by Treatment with Formol

The IL-10 is obtained from the IL-10 fusion protein by treatment with formol at 37° C. followed by a short treatment with glutaraldehyde, in accordance with the protocol described for the p53 immunogen. The IL-10 fusion protein was produced in *E. Coli* from a cDNA cloned in the prSetA bacterial expression plasmid and purified in the form of a fusion protein with Tag His. This purified fusion protein is homogenous in acrylamide electrophoresis and in Western blot.

Characteristics of the IL-10 Immunogen

The antigenicity of the treated IL-10 cytokine in comparison to that of the native recombinant protein was measured using an R&D ELISA test (D1000): The native and treated IL-10 cytokines present an equivalent antigenicity.

The absence of toxicity in vitro is measured by a cell proliferation test. The treated IL-10 cytokine used at doses 10 times and 30 times greater than the physiological doses does not modify the proliferation of mononucleated cells of human peripheral blood activated by SEB.

b) IL-10 Plasmid Immunogen For DNA Vaccination

The IL-10 plasmid immunogen is represented by a cDNA of cloned IL-10 in the prSetA bacterial expression plasmid.

Preparation 6: Anti TNFα Vaccine a) TNFα Immunogen Derived From TNFα By Chemical Treatment The immunogen derived from TNFα (Peprotech Inc., Rocky Hill) is obtained by treatment with formol at 37° C. followed by a short treatment with glutaraldehyde, in accordance with the protocol described for the p53 immunogen.

Characteristics of TNFα

The antigenicity of the treated TNFα cytokine in comparison to that of the native recombinant protein was measured using an R&D ELISA test (DTA50): The native and treated TNFα cytokines present an equivalent antigenicity.

The absence of toxicity in vitro is measured by a cell proliferation test. The treated TNFα cytokine used at doses 10 times and 30 times greater than the physiological doses does not modify the proliferation of mononucleated cells of human peripheral blood activated by SEB.

b) TNFα Plasmid Immunogen for DNA Vaccination

The TNFα plasmid immunogen is represented by a cDNA of cloned TNFα in the bacterial expression plasmid prSetA.

Preparation 7: IFNγ Immunogens a) The IFNγ Immunogen Derived from IFNγ

This immunogen (Peprotech Inc., Rocky Hill) is obtained by treatment with formol at 37° C. followed by a short treatment with glutaraldehyde, in accordance with the protocol described for the p53 immunogen.

Characteristics of the Immunogen:

The antigenicity of the treated IFNγ cytokine in comparison to that of the native recombinant protein was measured using an R&D ELISA test (DTA50): The native and treated IFNγ cytokines present an equivalent antigenicity.

The absence of toxicity in vitro is measured by a cell proliferation test. The treated IFNγ cytokine used at doses 10 times and 30 times greater than the physiological doses does not modify the proliferation of mononucleated cells of human peripheral blood activated by SEB.

b) IFNγ Plasmid Immunogen for DNA Vaccination

The IFNγ plasmid immunogen is represented by a cDNA of cloned IFNγ.

Preparation 8: KLH-SIAB-VEGF Immunogen

Conjugation of VEGF to the KLH protein, used as a carrier has the effect of potentializing the immunogenicity of VEGF.

The conjugation was carried out by reacting the reduced VEGF with KLH activated by treatment with sulfosuccinimidyl [4-iodoacetyl]aminobenzoate (called sulfo-SIAB).

Stage 1: Reduction of VEGF by DTT

40 μl of a solution of DTT (Dithiotreitol) at 50 mg/ml was added to 1 mg of VEGF in solution in 500 μl of PBS. The mixture was kept for 2 hours at ambient temperature, protected from the light, and the reaction mixture was filtered through a Sephadex G25 column (1×15 cm) equilibrated with PBS containing EDTA-$Na_2$ 5 mM, pH 7.0.

Stage 2: Treatment of KLH by Sulfo-SIAB

Sulfo-SIAB is a spacer arm which makes it possible to link the carrier protein, here KLH, with the VEGF immunogen in order to create a conjugate.

50 μl of borate buffer 0.1 M-EDTA $Na_2$-5 mM, pH 8.5 were added to 150 μl of a solution of KLH at 20 mg/ml, followed by the addition of 20 μl of a solution in water of sulfo-SIAB at 3.4 mg/ml, the reaction took place over 30 minutes at ambient temperature and protected from the light, under a nitrogen barrier. The reaction mixture was then filtered through a Sephadex G25 column (1×11 cm) equilibrated with the same buffer.

Stage 3: Conjugation of Reduced VEGF with KLH-SIAB 1 ml of solution of reduced VEGF was mixed with 500 μl of KLH-SIAB. The mixture was incubated, protected from the light and at ambient temperature, under nitrogen, for 1 hour, then for 15 hours at 4° C.

After the reaction was blocked by adding cysteine at a final concentration of 5 mM, over 20 minutes, the mixture was purified by exclusion chromatography.

Characteristics of the KLH-SIAB-VEGF Immunogen:

The antigenicity of the conjugated VEGF proved to be comparable to that of the isolated VEGF.

The absence of toxicity in vitro was measured by a cell proliferation test. The conjugated KLH-SIAB-VEGF used at doses 10 times and 30 times greater than the physiological doses does not modify the proliferation of mononucleated cells of human peripheral blood activated by SEB.

Preparation 9: KLH-SMCC-VEGF Immunogen

The conjugation of VEGF to the KLH protein, used as a carrier has the effect of potentializing the immunogenicity of VEGF.

Conjugation was carried out by reacting the reduced VEGF with the KLH activated by treatment with (sulfosuccinimidyl [4-N-maleimidomethyl]-cyclohexane-1-carboxylate) (sulfo-SMCC).

Stage 1: Reduction of VEGF by DTT

Sulfo-SMCC is a spacer arm which allows the carrier protein, here KLH, to be linked with VEGF in order to form a conjugate.

40 µl of a solution of DTT at 50 mg/ml was added to 1 mg of VEGF in solution in 500 µl of PBS. The mixture was kept for 2 hours at ambient temperature, protected from the light, and the reaction mixture was filtered through a Sephadex G25 column (1×15 cm) equilibrated with PBS containing EDTA-Na$_2$ 5 mM, pH 7.0.

Stage 2: Treatment of KLH by Sulfo-SMCC

50 µl of borate buffer 0.1 M-EDTA Na$_2$-5 mM, pH 8.5 was added to 150 µl of a solution of KLH at 20 mg/ml, followed by the addition of 20 µl of a solution in water of sulfo-SMCC at 3.4 mg/ml, the reaction took place over 30 minutes at ambient temperature and protected from the light, under a nitrogen barrier. The reaction mixture was then filtered through a Sephadex G25 column (1×11 cm) equilibrated with the same buffer.

Stage 3: Conjugation of reduced VEGF to KLH-SMCC 1 ml of a solution of reduced VEGF was mixed with 500 µl of KLH-SMCC. The mixture was incubated, protected from the light and at ambient temperature, under nitrogen, for 1 hour, then for 15 hours at 4° C.

After which the reaction was blocked by the addition of cysteine at a final concentration of 5 mM, over 20 min, the mixture was purified by exclusion chromatography.

Characteristics of the KLH-SMCC-VEGF Immunogen:

The antigenicity of conjugated VEGF proved to be comparable to that of isolated VEGF.

The absence of toxicity in vitro is measured by a cell proliferation test. The conjugated KLH-SMCC-VEGF used at doses 10 times and 30 times greater than the physiological doses does not modify the proliferation of mononucleated cells of human peripheral blood activated by SEB.

Preparation 10: KLH-Glutaraldehyde-VEGF Immunogen

The conjugation has the effect of potentializing the immunogenicity of the VEGF protein.

The conjugation was carried out by reacting the VEGF molecule with KLH activated by glutaraldehyde.

1 ml of a solution of KLH at 10 mg/ml in PBS was activated by dialysis against 100 ml of a glutaraldehyde solution at 0.2% in PBS, overnight, at 4° C. The excess glutaraldehyde was eliminated by dialysis of the activated protein against 3 changes of 200 ml of PBS of 2 hours each.

1 mg of a solution at 1 mg/ml of the VEGF protein in PBS is added to 400 µl of activated KLH (4 mg) and the reaction mixture is agitated, overnight, at 4° C. The free aldehyde groups are then blocked by reacting for 1 hour with 100 µl of 2.5 M glycine and the mixture is purified by exclusion chromatography. The antigenicity of the VEGF protein in the conjugate proved to be slightly greater than that of the isolated VEGF.

Preparation 11: KLH-Glutaraldehyde-E7 Immunogen

The conjugation has the effect of potentializing the immunogenicity of the E7 protein.

The conjugation was carried out by reacting the E7 molecule with KLH activated by glutaraldehyde starting with 1 ml of a solution of KLH at 10 mg/ml in PBS according to the same protocol as that described for Preparation 10.

The antigenicity of the E7 protein in the conjugate proved to be slightly greater than that of isolated E7.

Preparation 12: KLH-Glutaraldehyde-IFNα

The IFNα was conjugated to KLH under the same conditions as those described in Preparation 11 for the E7 protein.

The antigenicity of the conjugated IFNα proved to be slightly greater than that of IFNα treated with glutaraldehyde alone.

Pharmacological Study

A—Presence in the extracellular medium of malignant tumors, of molecules participating in the immunosuppression, the apoptosis or the angiogenesis of the microenvironment of cancerous cells.

Experiment A1:

The p53 protein which accumulates in malignant tumors and is present in the extracellular medium the serum of which (Zusman I, Sandier B, Gurevich P, Zusman R, Smirnoff P, Tendler Y, Bass D, Shani A, Idelevich E, Pfefferman R, Davidovich B, Huszar M, Glick J. Comparative study of the role of serum levels of p53 antigen and its tumor cell concentration in colon cancer detection. Hum Antibodies Hybridomas. (1996):123-8), activates the overproduction by the APC's of IFNα, mediator of immunosuppression, and TNFα, a cytokine participating in the expression of the adhesion molecules of the endothelial cells and the apoptosis of the immune cells.

Experimental Protocol

Macrophages, which originate from the differentiation of elutriated monocytes cultured for 5 days in teflon pouches in the presence of GMC-SF (F. Sallusto et al, Efficient presentation of soluble antigen by cultured human dendritic cells is maintained by granulocyte/macrophage colony-stimulating factor plus interleukin 4 and downregulated by tumor necrosis factor alpha. J Exp Med (1994) 179, 1109), are activated with LPS for 16 hours. These thus activated macrophages are then cultured in the presence of increasing doses (0-10 µg/ml) of the native recombinant p53 protein (sc-4246, Santa Cruz) and control protein) in a medium without serum for 24 hours. The control protein was the recombinant p24 protein (HIV-1 protein, ANRS origin).

Results:

Measurement of the APC overproduction of IFNα and TNFα in the culture supernatants (SN) of the APC's is carried out respectively by the standard biological test for IFNα, using the lysis of MDBK cells by VSV (S. Rubinstein et al, Convenient assay for interferons. J. Virol (1981) 37, 755) and by an R&D ELISA test (DTA50, R&D).

The titre of IFNα in the supernatants corresponds to the inverse of the stronger dilution of the supernatants inducing 50% protection of the cells against the cytopathic effect of VSV. Measurement of TNFα in the supernatants is carried out following the protocol described by the manufacturer and is expressed in pg/ml. The results are represented in the following table

|  | Titre of IFNα (dilution$^{-1}$) | TNFα (pg/ml) |
| --- | --- | --- |
| experimental p53 | | |
| 10 µg/ml | 128 | 8700 |
| 3 µg/ml | 64 | 6200 |
| 1 µg/ml | 32 | 5600 |
| 0.3 µg/ml | 12 | 2600 |
| 0.1 µg/ml | 6 | 1300 |
| 00 µg/ml | 2 | 200 |
| control p24 | | |
| 10 µg/ml | 2 | 250 |
| 3 µg/ml | 2 | 200 |
| 1 µg/ml | 2 | 200 |
| 0.3 µg/ml | 2 | 200 |
| 0.1 µg/ml | 2 | 200 |
| 00 µg/ml | 2 | 200 |

The native recombinant p53 protein induces the overproduction of IFNα and TNFα, whilst the recombinant p24 protein used in the controls does not induce any synthesis.

An insect cell culture lysate with baculovirus expressing the p53 protein gave similar results to those described for the recombinant p53 protein produced in *E. Coli*.

Experiment A2:

TGFβ cytokine, released in the extracellular medium by cancerous cells inhibits the proliferation of T cells and activates the production by the macrophages of IFNα, a major immunosuppressive cytokine.

Experimental Protocol

Mononucleated cells from human peripheral blood, isolated on a Ficoll gradient from the peripheral blood of a healthy subject, are cultured in the presence of the anti-CD3 antibody and in the presence of increasing doses (0-30 ng/ml) of the active recombinant TGFβ protein (240-B-002, R&D) and increasing doses (0-30 ng/ml) of a control protein, the recombinant p24 protein.

Inhibition of the proliferation of T cells is measured using a cell proliferation test (Lachgar A., Bernard J., Bizzini B., Astgen A., The Coq H., Fouchard M., Chams V., Feldman M., Richardson M., Rappaport J., Burny A. & J. F. Zagury: Repair of the in vitro HIV-1-induced immunosuppression and blockade of the generation of functional suppressive CD8 cells by anti-alpha interferon and anti-Tat antibodies. Biomed & Pharmacother. (1996) 50:13-18).

Activation of the production of IFNα by the macrophages is measured according to the protocol described in Experiment A1. The activated macrophages are cultured in the presence of increasing doses (0-1 µg/ml) of the active recombinant TGFβ protein and a control protein, the recombinant p24 protein, in a medium without serum for 24 hours.

Results:

Inhibition of cell proliferation by TGFβ:

Cell proliferation is expressed in % of cell proliferation ((control cpm/sample cpm)×100) at three concentrations (30, 10 and 3 ng/ml) of TGFβ and p24 protein. The control corresponds to a concentration of recombinant protein used equal to 0. The results are presented in FIG. 1:

These results show that cell proliferation is reduced in a dose-dependant manner by active TGFβ, whilst it is not by p24.

Activation by TGFβ of the overproduction of IFNα by the macrophages.

The titre of IFNα in the supernatants corresponds to the inverse of the stronger dilution of the supernatants inducing 50% protection against the cytopathic effect of VSV. The results are presented in the following table:

|  | Titre of IFNα |
|---|---|
| experimental TGFβ | |
| 1 µg/ml | 16 |
| 300 ng/ml | 8 |
| 100 ng/ml | 4 |
| 30 ng/ml | 2 |
| 00 ng/ml | 0 |
| control P24 | |
| 1 µg/ml | 0 |
| 300 ng/ml | 0 |
| 100 ng/ml | 0 |
| 30 ng/ml | 0 |
| 00 ng/ml | 0 |

The active recombinant TGFβ protein induces the overproduction of IFNα, whilst the recombinant p24 protein does not induce any synthesis.

Vaccination Experiment 1:

Anti-IL-10 vaccination of mice for the induction of a systemic and mucosal immunity with preferential formation of IgG and IgA class specific antibodies.

Immunization Protocol

Day 0: IM injection of a plasmid immunogen suspension expressing IL-10 (100 µg) in 0.2 ml of PBS prepared in Example 2.

Day 7, day 8, day 9: Administration by gavage of aqueous suspensions of microspheres (PLGA) including the IL-10 immunogen (100 µg/dose) and LTµ adjuvant (5 µg/dose).

The control mice receive the same preparations without immunogen.

Monitoring:

The animals are sacrificed 15 days after the last immunization and the absence of toxicity is noted (measured by the absence of clinical signs (behavior; coat; weight) and by anatomical examination after autopsy.

Immune reaction tested by the presence in the serum of IgG and IgA type antibodies, measured by ELISA and expressed by the optical density 15 days after the final gavage.

|  | Control mice (O.D) | Immunized mice (O.D) |
|---|---|---|
| IgG class anti IL-10 Ab | 0.2 | 0.920 |
| IgA class anti IL-10 Ab | 0.1 | 0.780 |

Results:

Clinical innocuousness and absence of anatomical lesions.

Presence of anti IL-10 of IgG and IgA type antibodies (Ab) in the serum.

Vaccination Experiment 2:

Anti-VEGF vaccination of mice by the induction of a systemic and mucosal immunity with preferential formation of IgG and IgA class specific antibodies.

Immunization Protocol

Day 0: IM injection of a suspension of VEGF immunogen (20 µg) in ISA 51 prepared in Example 1.

Day 7, day 14, day 21: Intranasal administration using a Hamilton pipette of 10 µl of an aqueous suspension containing 20 µg of immunogen and 5 µg of LTµ included in a calcium phosphate gel.

The control mice receive the same preparations without immunogen.

Monitoring:

The animals are sacrificed 15 days after the last immunization and the absence of toxicity is noted (measured by the absence of clinical signs (behavior; coat; weight) and by anatomical examination after autopsy.

Immune reaction tested by the presence in the serum of IgG and IgA type antibodies, measured by ELISA and expressed by the optical density 15 days after the last instillation.

|  | Control mice (O.D) | Immunized mice (O.D) |
|---|---|---|
| IgG class anti VEGF Ab | 0.27 | 1.64 |
| IgA class anti VEGF Ab | 0.15 | 1.118 |

Results:
    Clinical innocuousness and absence of anatomical lesions.
    Presence of IgG and IgA type anti VEGF antibodies in the serum.

Vaccination Experiment 3:
    Anti-p53 vaccination of mice by the induction of a systemic and mucosal immunity with preferential formation of IgG and IgA class specific antibodies.

Immunization Protocol
    Day 0: IM injection of a suspension of p53 immunogen (20 µg) in ISA 51 prepared as in Example 1.
    Day 7, day 14, day 21: Intranasal administration using a Hamilton pipette of 10 µl of an aqueous suspension containing 20 µg of immunogen and 5 µg of LTµ included in a calcium phosphate gel.

The control mice receive the same preparations without immunogen

Monitoring:
    The animals are sacrificed 15 days after the last immunization and the absence of toxicity is noted (measured by the absence of clinical signs (behavior; coat; weight) and by anatomical examination after autopsy.
    Immune reaction tested by the presence in the serum and in the saliva of IgG and IgA type antibodies, measured by ELISA and expressed by the optical density 15 days after the last instillation.

Results:
    Clinical innocuousness and absence of anatomical lesions.
    Presence of IgG and IgA type anti-p53 antibodies in the serum and in the saliva.

|  | Control mice (O.D) | Immunized mice (O.D) |
| --- | --- | --- |
| serum | | |
| IgG class anti-p53 Ab | 0.184 | 1.492 |
| IgA class anti-p53 Ab | 0.208 | 1.071 |
| saliva | | |
| IgG class anti-p53 Ab | 0.184 | 1.5 |
| IgA class anti-p53 Ab | 0.208 | 0.980 |

Vaccination Experiment 4:
    Anti IL-6 vaccination of mice for the induction of a systemic immunity with formation of IgG class specific antibodies.

Immunization Protocol
    Day 0: IM injection of a suspension of IL-6 immunogen (20 µg) in ISA 51 prepared as in Example 1.
    Day 21: Booster by IM route of an emulsion of IL-6 (5 µg) in ISA 51

The control mice receive the same preparations without immunogen.

Monitoring:
    The animals are sacrificed 15 days after the booster and the absence of toxicity is noted (measured by the absence of clinical signs (behavior; coat; weight) and by anatomical examination after autopsy.
    Immune reaction tested by the presence in the serum of IgG and IgA type antibodies, measured by ELISA and expressed by the optical density 7 days after the booster.

|  | Control mice (O.D) | Immunized mice (O.D) |
| --- | --- | --- |
| IgG class anti IL-6 Ab | 0.280 | 2.356 |
| IgA class anti IL-6 Ab | 0.230 | 0.320 |

Results:
    Clinical innocuousness and absence of anatomical lesions.
    Presence of IgG type anti IL-6 antibodies in the serum.

Vaccination Experiment 5:
    Anti IL-6 vaccination of mice by the induction of a systemic and mucosal immunity with preferential formation of IgG and IgA class specific antibodies.

Immunization Protocol
    Day 0: IM injection of a suspension of IL-6 immunogen (20 µg) in ISA 51 prepared as in Example 1.
    Day 7, day 8, day 9: Administration by gavage of PLG microspheres containing the immunogen (100 µg/dose) and LTµ adjuvant (5 µg/dose).

The control mice receive the same preparations without immunogen.

Monitoring:
    The animals are sacrificed 15 days after the final gavage and the absence of toxicity is noted (measured by the absence of clinical signs (behavior; coat; weight) and by anatomical examination after autopsy.
    Immune reaction tested by the presence in the serum of IgG and IgA type antibodies, measured by ELISA and expressed by the optical density 15 days after the final gavage.

|  | Control mice (O.D) | Immunized mice (O.D) |
| --- | --- | --- |
| IgG class anti IL-6 Ab | 0.250 | 1400 |
| IgA class anti IL-6 Ab | 0.175 | 1.62 |

Results:
    Clinical innocuousness and absence of anatomical lesions.
    Presence of IgG and IgA type anti IL-6 antibodies in the serum.

Vaccination Example 6: Anti-VEGF Vaccination with the Conjugated KLH-SIAB-VEGF
    The immunogenic (humoral) activity of the conjugated KLH-SIAB-VEGF conjugate in comparison to that of the native VEGF was studied in 18-20 g BALB/c mice.
    On day 0, a group of 3 mice received an injection of 0.2 ml (50 µg) of an emulsion in Freund's complete adjuvant by intramuscular route. A booster injection of 5 µg in Freund's incomplete adjuvant is given on day 21 and day 60.
    A blood sample is carried out at retro-orbital level on each mouse before the first injection on day—2
    3 control mice receive the same preparations without immunogen.
    3 mice receive 100 µg of the preparation and the absence of symptoms of disease is studied for the 7 days following the injection.
    The mice are sacrificed 12 days after the last immunization.
    The absence of toxicity is measured by the absence of clinical signs: (behavior, coat, weight) and by anatomical examination after autopsy.

Results:
    None of the 3 mice immunized with 100 µg of the preparation show symptoms of disease during the 7 days following the injection.

The mice immunized equally well by the conjugated KLH-SIAB-VEGF as VEGF alone do not present any clinical signs and anatomical lesions.

The immune reaction is measured by:
a) the presence in the serum of IgG type antibodies directed against the native recombinant VEGF protein, measured by ELISA and expressed as a titre (the inverse of the dilution giving an optical density greater than 0.3)

|  | Titre | |
|---|---|---|
|  | D-2 | D 72 |
| control mice: | | |
| mouse 1 | $<500^{-1}$ | $<500^{-1}$ |
| mouse 2 | $<500^{-1}$ | $<500^{-1}$ |
| mouse 3 | $<500^{-1}$ | $<500^{-1}$ |
| mice immunized with VEGF: | | |
| mouse 4 | $<500^{-1}$ | $500^{-1}$ |
| mouse 5 | $<500^{-1}$ | $1000^{-1}$ |
| mouse 6 | $<500^{-1}$ | $750^{-1}$ |
| mice immunized with the conjugated KLH-SIAB-VEGF: | | |
| mouse 7 | $<500^{-1}$ | $>64000^{-1}$ |
| mouse 8 | $<500^{-1}$ | $>64000^{-1}$ |
| mouse 9 | $<500^{-1}$ | $>64000^{-1}$ |

The mice immunized with the conjugated KLH-SIAB-VEGF present IgG type anti-VEGF antibody titres greater than those of mice immunized with VEGF alone.

Example 7

Comparison of Neutralizing Activities of Serums of Mice Immunized with the Conjugated KLH-SIAB-VEGF or with Native VEGF The neutralizing activity of these antibodies was measured using the standard biological test of VEGF activity. Different serum dilutions (1/100-1/800) taken on day—2 and day 72 are incubated for 2 hours with 10 ng/ml of native VEGF. These dilutions are then deposited onto endothelial (HU-VEC) cells cultured in flat-bottomed wells of a micro-culture plate at a rate of 3000 cells/well. The cell culture is continued at 37° C. in a humid atmosphere charged with 5% $CO_2$ for 6 days. 18 hours before the end of incubation, 0.5 µCi of tritiated thymidine/well is added.

The results are given in % neutralization.

|  |  | % neutralization | | | |
|---|---|---|---|---|---|
|  |  | 1/100 | 1/200 | 1/400 | 1/800 |
| Mice immunized with VEGF: | | | | | |
| mouse 4 | D-2 | 0 | 0 | 0 | 0 |
|  | D 72 | 15 | 0 | 0 | 0 |
| mouse 5 | D-2 | 0 | 0 | 0 | 0 |
|  | D 72 | 20 | 0 | 0 | 0 |
| mouse 6 | D-2 | 0 | 0 | 0 | 0 |
|  | D 72 | 15 | 0 | 0 | 0 |
| Mice immunized with KLH-VEGF | | | | | |
| mouse 7 | D-2 | 0 | 0 | 0 | 0 |
|  | D 72 | 100 | 100 | 100 | 100 |
| mouse 8 | D-2 | 0 | 0 | 0 | 0 |
|  | D 72 | 100 | 100 | 100 | 100 |
| mouse 9 | D-2 | 0 | 0 | 0 | 0 |
|  | D 72 | 100 | 100 | 100 | 100 |

The antibodies induced by the conjugated KLH-VEGF have a greater neutralizing power than that of the antibodies induced by VEGF.

Example 9

Comparison of the Neutralizing Activities of Mice Immunized with Either Native VEGF, or the Conjugated KLH-SIAB-VEGF, or Conjugated KLH-SMCC-VEGF, or the Conjugated KLH-Gluta-VEGF The neutralizing activity is determined according to the same experimental protocol as that described in Example 8. As in the experimentation protocol of Example 7, the mice were immunized on day 0, day 21 and day 60.

Figure 2:
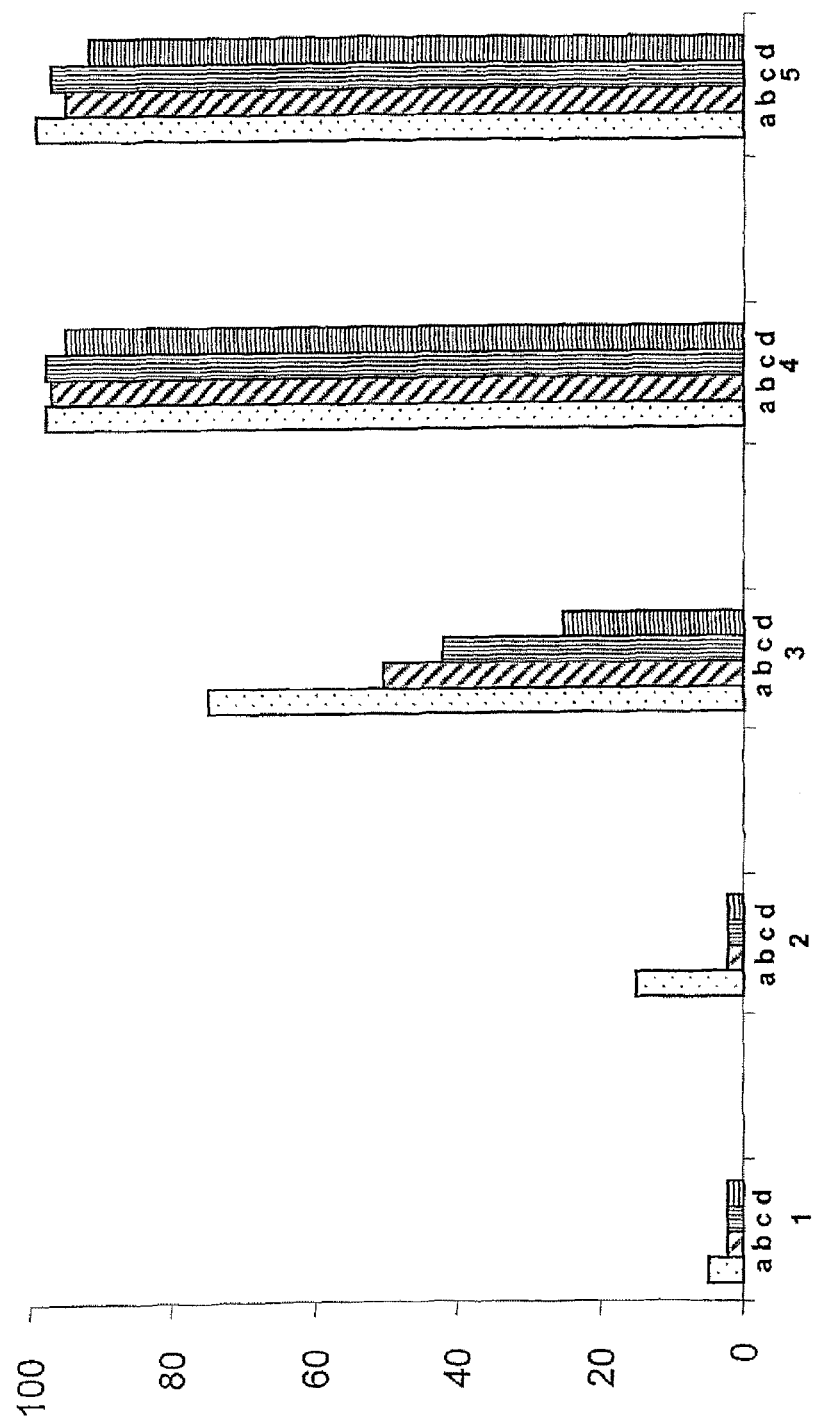
FIG. 2 shows the effect of mouse serum immunized with VEGF immunogen not conjugated or conjugated to KLH according to different conjugation techniques and at 4 different dilutions, (a) 1/100, (b) 1/200, (c) 1/400 and (d) 1/800, indicated at the top of the table. The experiments were carried out from left to right with (1) naive mice, (2) mice immunized with VEGF on day 60, (3) mice immunized with KLH-glutaraldehyde-VEGF pH 9 on day 60, (4) mice immunized with KLH-SMCC-VEGF on day 60, (5) mice immunized with KLH-SIAB-VEGF on day 60. The neutralization percentage is given on the Y axis.

FIG. 2 summarizes the results obtained: It can be seen that from day 30, significant neutralization appears for the conjugated KLH-SIAB-VEGF and conjugated KLH-SMCC-VEGF. It is necessary to wait until day 70 in order to obtain neutralization with the conjugated KLH-glutaraldehyde-VEGF. On the other hand, no neutralization is observed for the native VEGF.

Example 10

Vaccination with the Conjugated KLH-Glutaraldehyde-E7

The immunogenic (humoral and cell) activity of the conjugated KLH-E7 in comparison to that of the E7 protein were studied in 18-20 g BALB/c mice.

On day 0, a group of 3 mice receive an injection of 0.2 ml (50 µg) of an ACF emulsion by intramuscular route. A booster injection of 5 µg of AIF is given on day 21 and day 60.

A blood sample at retro-orbital level is carried out on each mouse before the first injection on day—2

3 control mice receive the same preparations without immunogen.

3 mice receive 100 µg of the preparation and the absence of symptoms of disease is studied during the 7 days following the injection.

The mice are sacrificed 12 days after the last immunization.

The absence of toxicity is measured by the absence of clinical signs: (behavior, coat, weight) and by anatomical examination after autopsy.

Results:

None of the 3 mice immunized with 100 µg of the preparation show symptoms of disease during the 7 days following the injection.

The mice immunized equally well by the conjugated KLH-E7 as the E7 protein alone do not present any clinical sign and no anatomic lesion.

The immune reaction is measured by:
1—the presence in the serum of IgG type antibodies directed against the native recombinant E7 protein, measured by ELISA and expressed as a titre (the inverse of the dilution giving an optical density greater than 0.3)

| Titre | | |
|---|---|---|
| | D-2 | D 72 |
| control mice: | | |
| mouse 1 | <500$^{-1}$ | <500$^{-1}$ |
| mouse 2 | <500$^{-1}$ | <500$^{-1}$ |
| mouse 3 | <500$^{-1}$ | <500$^{-1}$ |
| mice immunized with the E7 protein: | | |
| mouse 4 | <500$^{-1}$ | 32 000$^{-1}$ |
| mouse 5 | <500$^{-1}$ | 64 000$^{-1}$ |
| mouse 6 | <500$^{-1}$ | 48 000$^{-1}$ |
| mice immunized with the conjugated KLH-E7: | | |
| mouse 7 | <500$^{-1}$ | >64 000$^{-1}$ |
| mouse 8 | <500$^{-1}$ | >64 000$^{-1}$ |
| mouse 9 | <500$^{-1}$ | >64 000$^{-1}$ |

The mice immunized with the conjugated KLH-E7 present anti-E7 IgG type antibody titres greater than those of mice immunized with the E7 protein alone.

What is claimed is:

1. A pharmaceutical composition comprising:
an immunogenic compound selected from the group consisting of:
(i) an inactivated cytokine derived from a cytokine that naturally induces immunosuppression, cell apoptosis or angiogenesis, the said inactivated cytokine consisting of an inactivated TNFα that has been inactivated by a) subjecting native TNFα to a chemical treatment with formaldehyde and b) subjecting the treated TNFα obtained in step a) to a chemical treatment with glutaraldehyde; and
(ii) an inactive peptide fragment comprising from 8 to 110 consecutive amino acids of a cytokine that naturally induces immunosuppression, cell apoptosis or angiogenesis, the said inactive peptide fragment consisting of a peptide fragment from TNFα that has been inactivated by a) subjecting a TNFα peptide fragment to a chemical treatment with formaldehyde and b) subjecting the treated TNFα peptide fragment in step a) to a chemical treatment with glutaraldehyde; and
one or more pharmaceutical excipients.

2. An immunogenic composition comprising:
an immunogenic compound selected from the group consisting of:
(i) an inactivated cytokine derived from a cytokine that naturally induces immunosuppression, cell apoptosis or angiogenesis, the said inactivated cytokine consisting of a TNFα that has been inactivated by a) subjecting native TNFα to a chemical treatment by formaldehyde and b) subjecting the treated TNFα obtained in step a) to a chemical treatment with glutaraldehyde; and
(ii) an inactive peptide fragment comprising from 8 to 110 consecutive amino acids of a cytokine that naturally induces immunosuppression, cell apoptosis or angiogenesis, the said inactive peptide fragment consisting of a peptide fragment from TNFα that has been inactivated by a) subjecting a TNFα peptide fragment to a chemical treatment by formaldehyde, and b) subjecting the treated TNFα peptide fragment obtained at step a) to a chemical treatment with glutaraldehyde; and
one or more adjuvants of immunity.

3. A method for inducing, in a patient affected with a malignant tumor, a systemic or a mucosal immune response including the production of IgG or secretory IgA antibodies that neutralize the biological activity of the native form of TNFα, the said method comprising a step of administering to the said patient a pharmaceutical composition according to claim 1.

4. A method for inducing, in a patient affected with a malignant tumor, a systemic or a mucosal immune response including the production of IgG or secretory IgA antibodies that neutralize the biological activity of the native form of TNFα, the said method comprising a step of administering to the said patient an immunogenic composition according to claim 2.

* * * * *